US00PP10713P

United States Patent [19]

Dykstra

[11] Patent Number: Plant 10,713

[45] Date of Patent: Dec. 8, 1998

[54] GRANDIFLORA ROSE PLANT VARIETY NAMED 'WEKDYKSTRA'

[75] Inventor: A. Michael Dykstra, Canton, Mo.

[73] Assignee: Weeks Wholesale Rose Grower, Inc., Upland, Calif.

[21] Appl. No.: 832,475

[22] Filed: Apr. 2, 1997

[51] Int. Cl.[6] ..... A01H 5/00

[52] U.S. Cl. ..... Plt./11

[58] Field of Search ..... Plt./11, 12

*Primary Examiner*—Howard J. Locker

*Attorney, Agent, or Firm*—Christie, Parker & Hale, LLP

[57] ABSTRACT

A new plant variety of Grandiflora rose suitable for garden decoration, having flowers of deep pink and gold coloration.

1 Drawing Sheet

BACKGROUND OF THE INVENTION

This invention relates to a new and distinct variety of Grandiflora Rose. The varietal denomination of the new variety is 'Wekdykstra'.

It has as its seed parent the variety known as 'Burway', (U.S. Plant Pat. No. 5,827) and as its pollen parent the variety known as 'Aroyqueli' (U.S. Plant Pat. No. 5,177).

SUMMARY OF THE INVENTION

The plant is a bushy tall upright plant, suitable for outdoor garden decoration. Among the features which distinguish the new variety from other presently available and known commercial rose cultivars are the following combination of characteristics: its unusual fresh flower coloration of gold surrounded by cerise pink, its very long stems, its light green young foliage and its strong fruity fragrance. 'Wekdykstra' may be asexually propagated by cuttings, budding or grafting.

Asexual reproduction of the new variety by budding as performed in Kern County and Upland, Calif., shows that the foregoing and other distinguishing characteristics come true to form and are established and transmitted through succeeding propagations.

Comparison with Parents

The new rose may be distinguished from its seed parent, 'Burway' by the following combination of characteristics: whereas 'Wekdykstra' is classified as a Grandiflora and has a very tall upright habit, 'Burway' is classified as a Hybrid Tea and has a significantly shorter plant habit. 'Burway' bears fresh flowers of a blended yellow and orange coloration, whereas 'Wekdykstra' bears fresh flowers of a gold coloration surrounded by cerise pink.

The new variety may be distinguished from its pollen parent, 'Aroyqueli' by the following combination of characteristics: whereas 'Wekdykstra' bears very fragrant flowers of a gold and cerise pink coloration, 'Aroyqueli' bears only slightly fragrant flowers of a deep yellow coloration.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color values are based upon the Colour Chart of The Royal Horticultural Society of London, England, except where common terms of color definition are employed.

DESCRIPTION OF THE NEW VARIETY

The following description is of rose plants of the new cultivar grown outdoors in Upland, Calif. in the month of October. Phenotypic expression may vary with environmental, cultural and climatic conditions, as well as differences in conditions of light and soil.

Flower

The new variety bears its flowers sometimes singly, usually in clusters of four or more per stem. Flowers are borne in irregular flat to rounded clusters on long strong stems (about 46 to about 60 cms.). Outdoors, the plant blooms abundantly and nearly continuously during the growing season. The flowers have a moderately strong fruity fragrance.

Bud

The peduncle is of about 4.5 to about 6.5 cms., of heavy caliper and usually erect. It is moderately smooth, with some stipitate glands. Peduncle color is between 146B and 139B, sometimes lightly blushed on the side facing the sun with between 166A and 183B.

Before the calyx breaks, the bud is of about 1.6 to about 2 cms. in diameter at the widest point, about 2.2 to about 2.8 cms. in length, and pointed to ovoid in shape. The surface of the bud bears few stipitate glands and a slight glandular bloom, usually with slender entire to somewhat cut foliaceous parts extending beyond the tip of the bud equal to ¼ or more of its length. Bud color is between 146B and 139B.

The inner surface of the sepals is covered with fine wooly tomentum; sepal margins are lined with few stipitate glands and sometimes with slender foliaceous parts.

As the petals open, the bud is about 2.5 to about 3 cms. in diameter at the widest point, about 3 to about 3.5 cms. in length, and very pointed to ovoid in form. The color of the under surfaces of the newly opened petals is between 24B and 22B. At the point where the petal attaches, there is a zone of between 14B and 13B that suffuses into the predominant yellow-orange coloration. Areas that are exposed to the sun sometime blush to between 47A and 53B. The color of the upper surfaces of the newly opened petals is between 25B and 22B. At the point where the petal attaches, there is a moderately large zone of between 14A and 15C that suffuses into the predominant yellow-orange coloration. Areas that are exposed to the sun sometime blush to between 47B and 53C. The bud opens up well and is generally not prevented from opening by cold, hot or dry weather.

Bloom

When fully open, the bloom ranges from about 9 to about 11 cms. in diameter. Petalage is double with about 31 to 36 petals and about 3 to 7 petaloids arranged regularly. When partially open, the bloom form is moderately cupped to high centered, and the petals are somewhat spiraled to cupped with petal edges moderately rolled outward. When fully open, the bloom form is more cupped to full, and the petals are more loosely cupped to somewhat undulated with petal edges rolled slightly outward.

Petals

The substance of the petals is somewhat heavy and of medium thickness, with upper surfaces slightly satiny and under surfaces somewhat shiny to satiny. The outer petals are very nearly round in shape with rounded apices. The inner petals are nearly round to broadly obovate in shape with rounded apices.

Newly Opened Flower

The under surface of the outer, intermediate and inner petals is between 21C and 20B. At the point where the petal attaches, there is a zone of between 14C and 13B that suffuses into the predominant yellow-orange coloration.

The upper surface of the outer, intermediate and inner petals is between 21B and 22B. At the point where the petal attaches, there is a zone of between 14B and 13A that suffuses into the predominant yellow-orange coloration.

The outermost portion of the upper surface of the outer petals which has been exposed to the sun blushes to as deeply as between 60C and 53C. The intermediate petals show less of this blush color. The inner petals show none of this blush color.

The general tonality of the newly opened flower is between 21B and 22B at the central portion of the flower with the outermost petals blushed to between 60C and 53C.

Three Day Old Flower

The under surface of the outer and inner petals is between 20C and 16D. At the point where the petal attaches, there is a moderately small zone of between 12C and 10A that quickly suffuses into the predominant petal coloration.

The upper surface of the outer and inner petals is between 16D and 12D. At the point where the petal attaches, there is a zone of between 12B and 13C that quickly suffuses into yellow-orange coloration. Areas exposed to the sun blush to as deeply as between 60C and 53C.

The general tonality of the three day old flower is between 60C and 53C.

On the spent bloom, the petals usually drop off cleanly.

In October in Upland, Calif., blooms on the bush growing outdoors generally last from four to five or more days. Cut roses grown outdoors and kept at normal indoor living temperatures generally last from four to five days.

Male Reproductive Organs

Stamens are average in number (approximately 70) and are arranged regularly about the pistil; a few are mixed with petaloids. The filaments are moderately uneven in length, most with anthers. The anthers are somewhat small to medium for the class and all open approximately at the same time. Anther color is near 162A when immature and near 166A at maturity. Pollen is moderate to abundant and near 16B in color.

Female Reproductive Organs

Pistils vary in number (approximately 50). The styles are moderately short to uneven in length, average in caliper, and moderately bunched. Stigma and style color is near 3C. Ovaries are usually all enclosed in the calyx.

Hips are ovoid to globular in form, and near 24A in color when fully ripe. The hip surface is moderately smooth with thick fleshy walls. Seeds are average to many in number (approximately 8 to 15), and usually moderately large in size.

Foliage

The compound leaves are usually comprised of three to five or more leaflets and are borne abundantly. The leaves are about 8 to about 14 cms. in length and about 6.5 to about 12 cms. in width at the widest point, moderately heavy to leathery in texture, and matte in finish. The leaflets are about 3.5 to about 7 cms. in length and about 2.5 to about 4 cms. in width at the widest point, shaped very oval with acute apices and somewhat rounded to acute bases. Their margins are usually simply serrate.

The upper surface of the mature leaf is between 147A and 139A. The under surface of the mature leaf is between 191A and 138B. The upper and under surface of the young leaf is near 144A, sometimes very lightly suffused with between 178C and 173C. The under surface of the young leaf is between 191B and 138B, sometimes very lightly suffused with between 178C and 173C.

The rachis is average in caliper and moderately smooth. The upper side is grooved with some hairs and stipitate glands on the edges of the grooves. The under side of the rachis is moderately smooth with few stipitate glands and very small prickles.

The stipules are moderately short in length with somewhat narrow width, with short to medium straight points that may turn out at an angle of more than 45 degrees.

The plant displays an average degree of resistance to blackspot and rust as compared to other commercial varieties grown under comparable conditions in Upland, Calif.

Growth

The plant has a bushy upright tall habit (about 170 to about 220 cms. in height and about 90 to about 130 cms. spread at the widest point), with very full branching. It displays very vigorous growth and the canes are of moderately heavy caliper for the class.

The color of the major stems is between 146C and 152A. They bear few large and small prickles which vary from about 0.25 to about 0.6 cms in length. The prickles are almost straight, angled moderately downward, with a medium length and somewhat broad base; prickle color is near 165B.

The color of the branches is between 146B and 137B, sometimes blushed lightly on the side facing the sun with between 166A and 183B. They bear few large and small prickles which are of similar size and shape to the prickles on the major stems; prickle color is near 162A, sometimes heavily blushed with near 178A.

The color of the new shoots is near 144A, sometimes very lightly suffused with between 178C and 173C. They bear few large and small prickles which are of similar size and shape to the prickles on the major stems; prickle color is similar to the prickles on the branches.

I claim:

1. A new and distinct variety of Grandiflora rose plant substantially as described and illustrated herein.

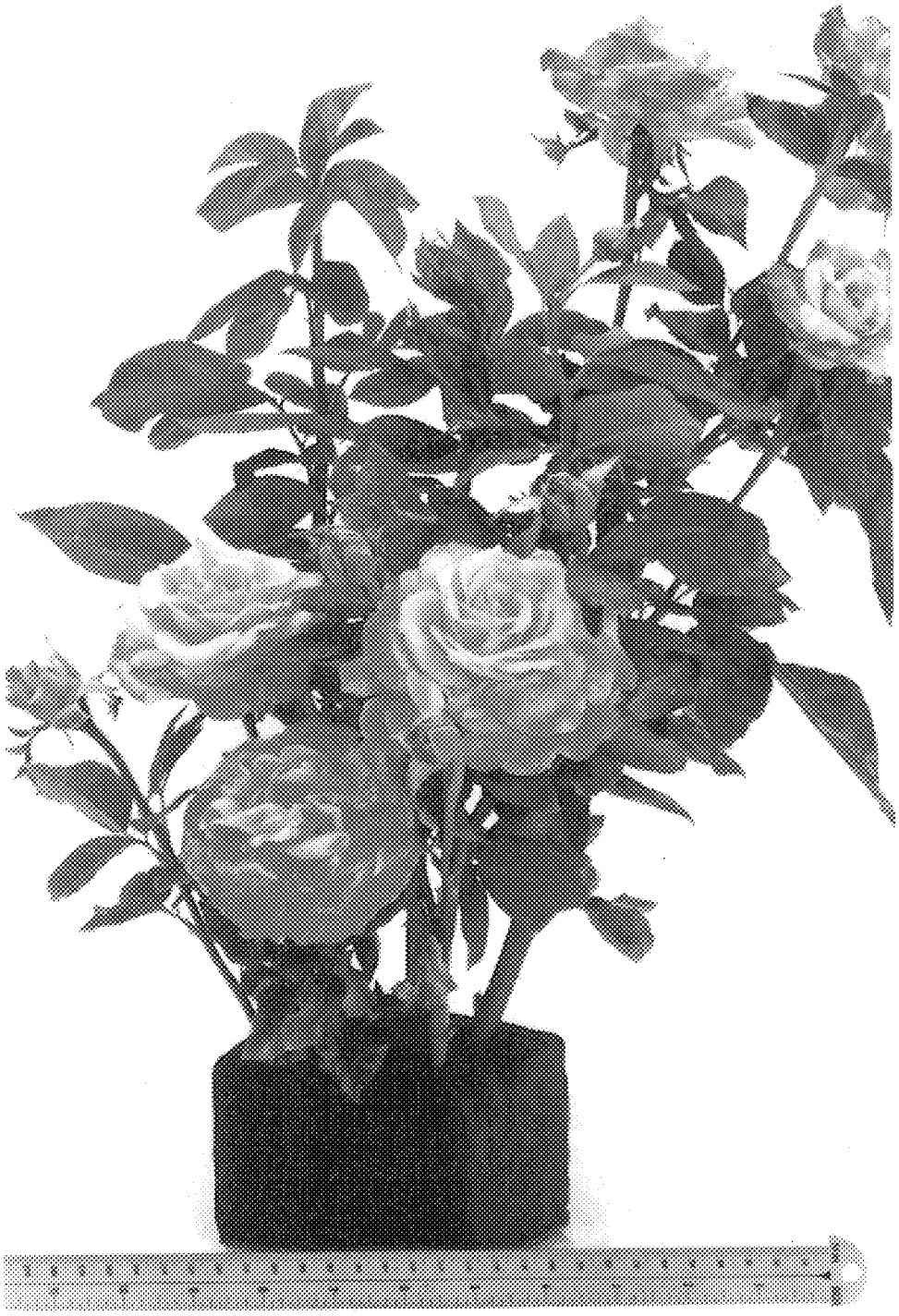

* * * * *